United States Patent [19]
Kojiri et al.

[11] Patent Number: 5,334,613
[45] Date of Patent: Aug. 2, 1994

[54] ANTIBACTERIAL SUBSTANCE BE-24566B

[75] Inventors: Katsuhisa Kojiri; Shigeru Nakajima; Aisaku Fuse; Hiroyuki Suda, all of Tsukuba, Japan

[73] Assignee: Banyu Pharmaceutical Co., Ltd., Tokyo, Japan

[21] Appl. No.: 974,460

[22] Filed: Nov. 12, 1992

[30] Foreign Application Priority Data

Nov. 12, 1991 [JP] Japan ................... 3-323699

[51] Int. Cl.⁵ .................... A01N 43/32; C07D 319/08
[52] U.S. Cl. ...................... 514/452; 549/358
[58] Field of Search ................ 549/358; 514/452

[56] References Cited
PUBLICATIONS

Oguri, et al.; "Clinic and Microorganisms"; 1988, 15; pp. 7–15.

*Primary Examiner*—Nicky Chan
*Attorney, Agent, or Firm*—Townsend & Banta

[57] ABSTRACT

Herein disclosed are an antibacterial substance: BE-24566B represented by the following structural formula (I):

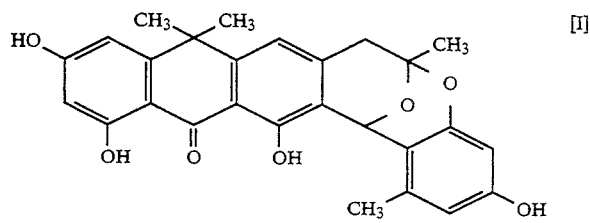

or a pharmaceutically acceptable salt thereof; and an antibacterial agent comprising, as an essential component, the foregoing antibacterial substance: BE-24566B or a pharmaceutically acceptable salt thereof. The antibacterial substance BE-24566B or pharmaceutically acceptable salts thereof can be prepared according to a method comprising the steps of inoculating an antibacterial substance: BE-24566B-producing microorganism or a variant thereof into a culture medium to cultivate the microorganism or variant, in particular the strain FERM BP-3994 or a variant thereof, and isolating the intracellularly and/or extracellularly produced antibacterial substance. The substance BE-24566B exhibits potent antibacterial effect on gram-positive bacteria represented by methicillin-resistant *Staphylococcus aureus* and, therefore, very useful as a therapeutic agent for treating a variety of infectious diseases caused by gram-positive bacteria.

2 Claims, No Drawings

ANTIBACTERIAL SUBSTANCE BE-24566B

BACKGROUND OF THE INVENTION

1. Field of the Invention

The present invention relates to a novel compound useful in the field of medicine and more specifically to a novel compound which can inhibit the proliferation of microorganisms and show antibacterial effect as well as a method for preparing the compound, an antibacterial agent containing the compound or a pharmaceutically acceptable salt thereof as an essential component and novel microorganisms belonging to the genus Streptomyces.

2. Description of the Prior Art

*Staphylococcus aureus* is known as a causative bacillus of suppurative diseases. This is clinically isolated in the highest frequency among the strains originated from outpatients, while this is second to *Pseudomonas aeruginosa* in the isolation-frequency among the strains originated from inpatients. Moreover, the infection in a hospital with multiresistant bacteria such as methycillin-resistant *Staphylococcus aureus* (MRSA) has often been observed and becomes a serious problem in large hospitals which have patients with advanced diseases. It has, in general, been known that the MRSA includes a large number of strains resistant to β-lactam antibiotics as well as a large number of strains resistant to antibiotics other than the β-lactam antibiotics such as gentamicin (GM), tobramycin (TOB), erythromycin (EM) and clindamycin (CLDM) (see, for instance. OGURI et al., "Rinsho To Biseibutsu (Clinic and Microorganisms)", 1988, 15, pp. 7–15). Under such circumstances, there has long been desired an antibacterial agent effective for controlling or inhibiting the MRSA.

SUMMARY OF THE INVENTION

Accordingly, an object of the present invention is to provide a compound exerting excellent antibiotic effect on the multiresistant MRSA which cannot satisfactorily be controlled or suppressed by the existing antibacterial agents.

Another object of the present invention is to provide a method for preparing the compound showing excellent antibiotic effect on the multiresistant MRSA.

A further object of the present invention is to provide a pharmaceutical composition comprising the compound as an essential component.

A still other object of the present invention is to provide a novel microorganism or a variant thereof having an ability of producing the compound.

To accomplish the foregoing objects the inventors of this invention have performed wide screening of microorganisms for substances exhibiting antibacterial activity and have found that the compound represented by the following structural formula (I) exhibits excellent antibacterial effects.

According to an aspect of the present invention, there is provided a compound represented by the following structural formula (I) (hereinafter referred to as "antibacterial substance BE-24566B"):

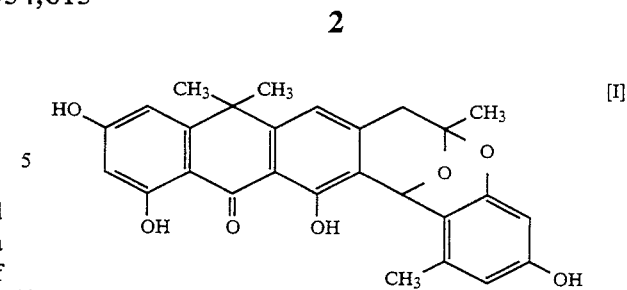

and pharmaceutically acceptable salts thereof.

According to another aspect of the present invention, there is provided an antibacterial agent which comprises, as an essential component, the antibacterial substance BE-24566B or a pharmaceutically acceptable salt thereof.

According to a further aspect of the present invention, there is provided a method for preparing the antibacterial substance BE-24566B or a pharmaceutically acceptable salt thereof which comprises subjecting a microorganism having an ability of producing the antibacterial substance BE-24566B or a variant thereof to a pure culture to thus allow accumulation of the substance BE-24566B in the culture medium and in the mycelium and then isolating the antibacterial substance BE-24566B.

According to a still further aspect of the present invention, there is provided a microorganism or a variant thereof which has an ability of producing the antibacterial substance BE-24566B and which belongs to the genus Streptomyces.

DETAILED EXPLANATION OF THE INVENTION

The present invention will become more apparent from the following detailed description.

The antibacterial substance BE-24566B has the following physicochemical properties:

(1) Appearance: Pale yellow amorphous solid or crystal (2) Molecular Formula: $C_{27}H_{24}O_7$ (3) Elemental Analysis: Calculated C 70.42%; H 5.25% Found C 70.36%; H 5.28%

(4) Melting Point: The compound is browned at around 160° to 170° C., but does not show any clear melting point.

(5) Mass Spectra: High Resolution FAB-MS: m/z 461.1611 $[M+H]^+$ (6) UV Spectra: λ [MeOH, max, nm(ε)] 204 (56,600), 220 (sh., 35,000), 273 (9,200), 360 (18,900)

(7) IR Spectra (KBr, $cm^{-1}$): 3418, 1470, 1365, 1290, 1230, 1143, 1029, 1611, 1431, 1326, 1254, 1170, 1056, 834

(8) $^1$H-NMR Spectra (acetone-$d_6$, δ ppm): 13.5 (1H, br. s), 12.8 (1H, br. s), 7.13 (1H, br. s), 6.74 (1H, d, J=2.1 Hz) 6.31 (1H, d, J=2.1 Hz), 6.26 (1H, d, J=2.5 Hz), 6.24 (1H, s), 6.15 (1H, d, J=2.5 Hz), 3.32 (1H, d, J=8.4 Hz), 3.13 (1H, d, J=8.4 Hz), 2.44 (3H, s), 1.67 (3H, s), 1.64 (3H, s), 1.60 (3H, s).

(9) $^{13}$C-NMR Spectra (acetone-$d_6$, δ ppm): 190.6 (s), 165.7 (s), 165.6 (s), 157.6 (s), 156.9 (s), 154.8 (s), 152.4 (s), 150.3 (s), 141.9 (s), 136.0 (s), 123.6 (s), 117.4 (d), 113.8 (s), 111.3 (s), 110.0 (d), 107.0 (s), 106.5 (d), 101.1 (d), 100.8 (d), 97.7 (s), 65.0 (d), 40.1 (t), 38.6 (s), 33.3 (q), 33.2 (q), 27.1 (q), 18.7 (q).

(10) Solubility: The compound is soluble in organic solvents such as methanol and dimethylsulfoxide, but hardly soluble in water.

(11) Acidity, Neutrality or Alkalinity: The compound is a weakly acidic substance.

(12) Rf Value: 0.5 (Kiesel Gel 60 available from Merck Company; developing solvent: 10:1 chloroform/methanol mixture).

(13) Color Reaction: Potassium permanganate reaction positive Sulfuric acid reaction positive

(14) Antibacterial Effect of the BE-24566B

The antibacterial effect was determined by the minimum inhibitory concentration (MIC) method. The results obtained are listed in the following Table 1.

TABLE 1

| Microorganism Tested | MIC (μg/ml) |
| --- | --- |
| *Bacillus subtilis*: ATCC 6633 | 1.56 |
| *Bacillus cereus*: IFO 3001 | 1.56 |
| *Staphylococcus aureus*: FDA 209P | 1.56 |
| *Staphylococcus aureus*: Smith | 3.13 |
| *Micrococcus luteus*: ATCC 9341 | 1.56 |
| *Enterococcus faecalis*: IFO 12580 | 3.13 |
| *Streptococcus thermophilus*: IFO 3535 | 3.13 |
| (MRSA) BB 6152 | 3.13 |

The data listed in Table 1 shows that BE-24566B according to the present invention can satisfactorily inhibit the proliferation of gram-positive bacteria represented by *Bacillus subtilis*. Consequently, the compound of the present invention is useful as a therapeutic agent for treating patients suffering from infectious diseases generally caused by gram-positive bacteria.

The antibacterial substance BE-24566B according to the present invention can be prepared by the following method.

The inventors of this invention isolated the substance BE-24566B from the culture of Actinomycetes (hereinafter referred to as strain "A24566") belonging to the genus Streptomyces which was separated and isolated from the soil sample collected in Jogasaki, Shizuoka Prefecture, Japan.

Mycological properties of the BE-24566B-producing microoganism (strain A24566) will be described below.

1. Morphology

The strain A24566 formed sufficiently developed and branching substrate mycelia and aerial mycelia and verticils and fragmentation of the substrate mycelia thereof were not observed. The strain formed linkages of the spores on the aerial mycelia and the linkage had a spiral form. The surface of the spores wrinkles and any particular organ such as sporangia, flagellar spores and sclerotia were not observed. When the strain was cultured on an oatmeal-agar culture medium, it was observed that the colony thereof gradually became moist and turns black as the aerial mycelia grew.

2 Growing Behavior on Various Agar Plate Culture Media

The strain was cultured on a variety of agar plate culture media at 28° C. for 14 days. The results obtained are hereinafter summarized.

a) Yeast-Malt-Agar Culture Medium (ISP-2): The strain quite satisfactorily grew. It satisfactorily formed brownish gray-colored aerial mycelia. It formed deep orange-yellow-colored substrate mycelia. It did not form any soluble dye.

b) Oatmeal-Agar Culture Medium (ISP-3): The strain quite satisfactorily grew. It formed deep grayish brown-colored aerial mycelia and deep grayish brown-colored substrate mycelia. It did not form any soluble dye.

c) Starch-Inorganic Salt-Agar Culture Medium (ISP-4): The strain quite satisfactorily grew. It formed deep grayish brown-colored aerial mycelia and pale olive-brown-colored substrate mycelia. It did not form any soluble dye.

d) Glycerin-Asparagine-Agar Culture Medium (ISP-5): The strain satisfactorily grew. It formed yellowish gray-colored aerial mycelia and pale yellow colored substrate mycelia. It did not form any soluble dye.

e) Peptone-Yeast-Iron-Agar Medium (ISP-6): The strain insufficiently grew. It only slightly formed aerial mycelia and formed pale brown-colored substrate mycelia. It did not form any soluble dye.

f) Tyrosine-Agar Medium (ISP-7): The strain insufficiently grew. It formed pale brownish gray-colored aerial mycelia and pale yellow-colored substrate mycelia. It did not form any soluble dye.

g) Nutrient-Agar Medium: The strain insufficiently grew. It did not form aerial mycelia and forms yellowish white-colored substrate mycelia. It did not form any soluble dye.

h) Sucrose-Nitrate-Agar Medium: The strain satisfactorily grew. It formed yellowish white-colored aerial mycelia and brilliant yellow-colored substrate mycelia. It did not form any soluble dye.

i) Glucose-Asparagine-Agar Medium: The strain insufficiently grew. It only slightly formed aerial mycelia and formed pale yellow colored substrate mycelia. It did not form any soluble dye.

3. Growth Temperature (The strain was cultured on an yeast-malt-agar medium for 14 days):

10° C.: It did not grow.

15° C.: It grew, but insufficiently formed aerial mycelia.

21° C.: It grew and satisfactorily formed aerial mycelia.

26° C.: It grew and quite satisfactorily formed aerial mycelia.

32° C.: It grew and quite satisfactorily formed aerial mycelia.

38° C.: It grew and quite satisfactorily formed aerial mycelia.

41° C.: It grew and satisfactorily formed aerial mycelia.

44° C.: It grew, but insufficiently formed aerial mycelia.

48° C.: It did not grow.

4. Physiological Properties:

(1) Liquefaction of Gelatin (glucose-peptone-gelatin medium): +

(2) Hydrolysis of Starch (starch-inorganic salt-agar medium): +

(3) Coagulation of Skimmed Milk (skimmed milk medium): −

(4) Conversion of Skimmed milk into Peptone (skimmed milk medium): +

(5) Formation of Melanin-Like Dye: −

(6) Resistance to Common Salt (yeast-malt-agar medium): The strain grew at a common salt concentration of not more than 7%.

5. Utilization of Carbon Source:

The strain was cultured on a medium mainly comprising Pridham Gottlieb agar as a basic medium to which a variety of sugars were added, at 28° C. for 14 days. The results thus obtained are summarized in the following Table 2.

TABLE 2

| D-glucose | + | raffinose | + |
|---|---|---|---|
| D-xylose | + | D-mannitol | + |
| L-arabinose | + | inositol | ± |
| L-rhamnose | + | salicin | − |
| D-fructose | + | sucrose | + |
| D-galactose | + | | |

6. Cell Wall Composition

LL-Diaminopimelic acid was detected in the cell wall thereof.

The BE-24566B-producing microorganism: A24566 strain is classified as the genus Streptomyces in the light of the foregoing mycological properties. Thus, the A24566 strain is herein referred to as "Streptomyces sp. A24566".

The strain is deposited with Fermentation Research Institute (FRI) under the accession number of FERM P-12080 and is deposited therewith under the Budapest Treaty at the accession number of FERM BP-3994.

The variants of the antibacterial substance BE-24566B-producing microorganism used in the present invention can be obtained by inducing mutation of the BE-24566B-producing microorganism according to the commonly used strain-conversion treatments such as irradiation with radiant rays (e.g., X-rays or ultraviolet rays); treatments with a mutation inducer such as nitrogen mustard, azaserine, nitrous acid, 2-aminopurine or N-methyl-N'-nitro-N-nitrosoguanidine (NTG); phage conversion; transformation; transduction; or conjugation.

The antibacterial substance BE-24566B can be prepared by inoculating the BE-24566B-producing microorganism such as the strain: A24566 or a variant thereof into a culture medium containing nutrients and cultivating the strain or the variant under aerobic conditions to give culture medium containing the antibacterial substance BE-24566B. The nutrients usable in the invention may be any known ones for Actinomycetes such as commercially available grape sugar (glucose), glycerin, malt sugar, straches, cane sugar, molasses, dextrin and mixture thereof for carbon sources; and commercially available powdered soybean, corn gluten meal, corn steep liquor, meat extract, degreased meat bone powder, meat meal, yeast extract, dry yeast, cottonseed oil, peptone, wheat germ, degreased rice bran, fish meal, inorganic ammonium salts, sodium nitrate or mixture thereof for nitrogen sources. Examples of inorganic salts usable in the present invention include commercially available calcium carbonate, calcium chloride, sodium chloride, sodium bromide, potassium chloride, magnesium sulfate and a variety of phosphates. The culture medium may optionally comprise trace amounts of heavy metal salts such as iron, manganese, cobalt, molybdenum, copper and/or zinc salts in addition to the foregoing essential ingredients. When the cultivation accompanies severe foaming, it is possible to add, to the culture medium, additives such as plant's oils (e.g., soybean oil and linseed oil); higher alcohols (e.g., octadecanol); and/or a variety of silicon atom-containing compounds as an anti-foaming agent according to need. In addition to the foregoing ingredients, any substances can be added to the culture medium so far as they are utilized by the BE-24566B-producing microorganism and effective for the production of the antibacterial substance BE-24566B. Examples of such substances include 3-(N-morpholino) propanesulfonic acid and sodium borate.

The cultivation of the strain A24566 and variants thereof may be performed in accordance with the commonly used methods for the production of microorganisms' metabolites such as solid culture and liquid culture methods. Examples of the liquid culture include stationary culture, spinner culture and shaking culture, with the shaking culture and submerged aeration-agitation culture being particularly preferred. The cultivation temperature appropriately ranges from 20° to 37° C. and preferably 25° to 30° C. The pH value of the culture medium preferably ranges from 4 to 8 and the cultivation time generally ranges from 48 to 168 hours and preferably 96 to 144 hours.

Methods for isolation of the antibacterial substance BE-24566B thus produced and accumulated in the cultures or Mycelium can be appropriately selected from any separation means usually adopted for harvesting metabolites from cultured microorganisms. The antibacterial substance BE-24566B is present in the filtrate of the culture and the Mycelium and thus the BE-24566B can be isolated from the filtrate of the culture medium and Mycelium through the usual separation means such as solvent-extraction methods, ion-exchange resin methods, adsorption or partition chromatography methods, gel-filtration methods and any combination thereof. In addition, high performance liquid chromatography and thin layer chromatography techniques may likewise be used in the extraction and purification processes.

If the compound of the present invention is used as an antibacterial agent, the compound may likewise be used in the form of pharmaceutically acceptable salts thereof. Typical examples of such pharmaceutically acceptable salts are salts with inorganic bases such as sodium hydroxide and potassium hydroxide.

If the compound of the present invention is used as an antibacterial agent, the antibacterial agent can be administered in a variety of dosage forms such as tablets, capsules, powders, granules, liquid preparations for oral administration; and liquid preparations such as solutions and suspensions for parenteral administration.

The compound of the present invention is used in the form of solid preparations, the compound per se can be formed into tablets, capsules, granules or powders, but the antibacterial agent of the present invention may further comprise various proper additives, for instance, sugars such as lactose and glucose; starches such as those originated from corn, wheat and rice; fatty acids such as stearic acid; inorganic salts such as aluminium magnesium metasilicate and anhydrous calcium phosphate; synthetic polymeric materials such as polyvinyl pyrrolidone and polyalkylene glycol; fatty acid salts such as calcium stearate and magnesium stearate; alcohols such as stearyl alcohol and benzyl alcohol; synthetic cellulose derivatives such as methyl cellulose, carboxymethyl cellulose, ethyl cellulose and hydroxypropyl methyl cellulose; and other additives commonly used in pharmaceutical preparations such as water, gelatin, talc, vegetable oils and gum arabic. These solid preparations such as tablets, capsules, powders and granules in general comprise the compound of the present invention as an essential component in an amount ranging from 0.1 to 100% by weight and preferably 5 to 100% by weight on the basis of the total weight of the solid preparation.

The liquid preparations can be prepared in the form of, for instance, suspensions, syrups and liquids for injection using proper additives commonly used in liquid preparations such as water, alcohols or oils originated from plants, for instance, soybean oil, peanut oil and sesame oil.

Examples of preferred solvents used for the preparation of drugs parenterally administered through intramuscular injection, intravenous injection or subcutaneous injection include distilled water for injection, lidocaine hydrochloride aqueous solution (for intramuscular injection), physiological saline, an aqueous solution of glucose, ethanol, liquids for intravenous injection (such as aqueous solutions of citric acid and sodium citrate), electrolyte solutions (for intravenous drip infusion and intravenous injection) and mixtures thereof.

These injections may be in the form of solutions in proper solvents or may be in powder form to which proper additives are optionally added. The latter is dissolved in a proper solvent prior to practical use. These solutions for injection in general comprise the compound of the present invention as an essential component in an amount of 0.1 to 10% by weight and preferably 1 to 5% by weight on the basis of the total weight of the preparation.

In addition, suspensions and syrups for oral administration may comprise the effective component in an amount ranging from 0.5 to 10% by weight on the basis of the total weight of the preparation.

It should be recognized that the practically preferred dose of the compound according to the present invention varies depending on the kinds of the compounds used and antibacterial agents prepared, the frequency of administration, particular sites to be treated and the subject to be treated. For instance, the dose to be administered per day for adult ranges from 10 to 500 mg for oral administration and 10 to 100 mg per day for parenteral administration, preferably intravenous injection. The frequency of administration may vary depending on the route of administration and conditions of patients to be treated, but in general ranges from 1 to 5 times per day for adult.

The present invention will be explained in more detail with reference to the following working Examples, but the present invention is by no means limited to these specific Examples.

EXAMPLE 1

The strain A24566 which had been cultured on a slant agar culture medium was inoculated into four 500 ml volume Erlenmeyer flasks for cultivation which contained 100 ml of culture medium comprising 0.2% glucose, 2.0% dextrin, 0.5% meat meal, 0.5% degreased rice bran, 0.2% degreased meat bone powder, 0.1% dry yeast, 0.05% magnesium sulfate, 0.05% sodium bromide, 0.5% sodium chloride, 0.1% potassium hydrogen phosphate, 0.2% calcium chloride, 0.004% cuprous chloride, 0.004% manganese chloride, 0.004% cobalt chloride, 0.008% zinc sulfate, 0.008% sodium borate, 0.024% ammonium molybdate and 0.02% ferrous sulfate and cultured on a rotary shaker (number of revolution of 180 rpm) at 28° C. for 72 hours. The cultured solution (2 ml each) was inoculated into 500 ml volume Erlenmeyer flasks (100 flasks) each containing 100 ml of the foregoing culture medium and cultured on a rotary shaker (number of revolution of 180 rpm) at 28° C. for 120 hours.

The culture medium (about 10 l) obtained through the cultivation of the strain was filtered to give Mycelium. Methanol (8 l) was added to the resulting Mycelium, and stirred at room temperature for 30 minutes, then the Mycelium was filtered off to give a methanol extract. The resulting methanol extract was concentrated to about 1 l under reduced pressure and then 1.5 l of ethyl acetate was added to the concentrate to perform extraction. Ethyl acetate (0.7 l) was added to the resulting aqueous layer to perform an additional extraction and the ethyl acetate extracts were combined to give about 2.7 l of ethyl acetate extract. The extract was washed twice with water (1 l each), and concentrated under reduced pressure. 1.5 l of ethyl acetate and 0.7 l of deionized water were added to the residue to extract the active component in the ethyl acetate layer. The aqueous layer was further extracted twice with ethyl acetate (1 l each) to give about 3 l of ethyl acetate extract in all and then anhydrous sodium sulfate was added to the extract. Subsequently, the ethyl acetate was distilled off under reduced pressure, and 240 ml of methanol and 400 ml of n-hexane were added to extract the resulting residue in the methanol layer. The remaining n-hexane layer was further extracted with 50 ml of methanol to give about 500 ml of methanol extract in all. The methanol extract was concentrated under reduced pressure, and then the resulting residue was dissolved in 200 ml of chloroform and applied on a silica gel column (3×48 cm). The elution was carried out according to the gradient elution using a chloroform/ethyl acetate mixed solvent (20:1→1:1) as an eluant and the resulting fractions containing the active component were concentrated to dryness under reduced pressure. The resulting crude powder of the substance BE-24566B was dissolved in 10 ml of methanol, and chromatographed on a Sephadex LH-20 column (2×88 cm) (eluant used: methanol) to give fractions exclusively containing the substance BE-24566B. These fractions containing the substance BE-24566B were concentrated under reduced pressure to give 209.6 mg of the substance BE-24566B as pale yellow powder.

As has been explained above in detail, the substance BE-24566B according to the present invention exhibits potent antibacterial effect on gram-positive bacteria represented by methicillin-resistant *Staphylococcus aureus* and, therefore, is very useful as a therapeutic agent for treating a variety of infectious diseases caused by gram-positive bacteria.

What is claimed is:

1. An antibacterial substance: BE-24566B represented by the following structural formula (I):

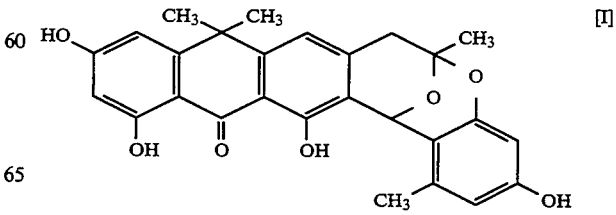

or a pharmaceutically acceptable salt thereof.

2. A pharmaceutical composition comprising, as an essential component, an antibacterial substance: BE-24566B represented by the following structural formula (I):
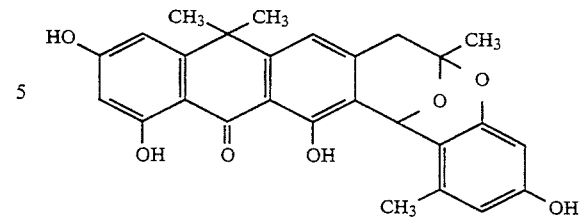
or a pharmaceutically acceptable salt thereof and a pharmaceutically acceptable carrier.
* * * * *